United States Patent [19]

Glasebrook

[11] Patent Number: 5,434,166

[45] Date of Patent: Jul. 18, 1995

[54] METHODS OF INHIBITING DEMYELINATING AND DESMYELINATING DISEASES

[75] Inventor: Andrew L. Glasebrook, Zionsville, Ind.

[73] Assignee: Eli Lilly and Company, Indianapolis, Ind.

[21] Appl. No.: 294,238

[22] Filed: Aug. 22, 1994

[51] Int. Cl.$^6$ .................. A61K 31/56; A61K 31/385
[52] U.S. Cl. .................. 514/317; 514/315; 514/422; 514/428; 514/438; 514/443; 514/444; 514/903
[58] Field of Search ............... 514/438, 443, 903, 444, 514/422, 317, 428, 315

[56] References Cited

U.S. PATENT DOCUMENTS

| | | |
|---|---|---|
| 4,133,814 | 1/1979 | Jones et al. |
| 4,380,635 | 4/1983 | Peters. |
| 4,418,068 | 11/1983 | Jones. |
| 5,075,321 | 12/1991 | Schreiber ............... 514/317 |

FOREIGN PATENT DOCUMENTS

| | | |
|---|---|---|
| WO93/10113 | 5/1993 | WIPO. |
| WO93/1074 | 6/1993 | WIPO. |

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18-22, 1993.

Bryant et al., "Raloxifene is a Tissue Specific Estrogen Agonist", Am Soc. Bone & Min. Res., Tampa, Sep. 18-22, 1993.

Frolick et al., "In Vivo and In Vitro Metabolism of Raloxifene", Am. Soc. Bone & Min. Res., Tampa, Sep. 18-22, 1993.

Glasebrook et al., "Multiple Binding Sites for the Anti--estrogen Raloxifene", Am Soc. Bone & Min. Res., Tampa, Sep. 18-22, 1993.

Hock et al., "Combination of Raloxifene and Human Parathyoid Hormone 1-34; Increased Femur Bone Mass in Young Ovariectomized (OVX) Rats", Am. Soc. Bone & Min. Res., Tampa, Sep. 18-22, 1993.

Sato et al., "DEXA Analysis of Raloxifene Effects on the Bones From Overariectomized Rats", Am. Soc. for Bone and Min. Res., Tampa, Sep. 18-22, 1993.

(List continued on next page.)

Primary Examiner—Marianne M. Cintins
Assistant Examiner—T. J. Criares
Attorney, Agent, or Firm—James J. Sales; David E. Boone; Gerald V. Dahling

[57] ABSTRACT

A method of inhibiting demyelinating or dysmyelinating diseases or their symptoms comprising administering to a human in need thereof an effective amount of a compound having the formula

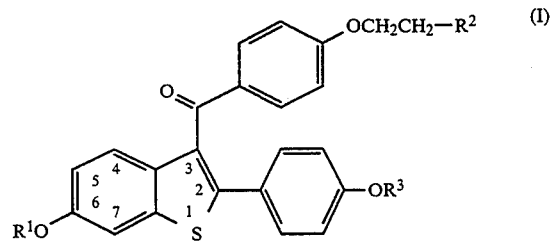

wherein $R^1$ and $R^3$ are independently hydrogen, —CH$_3$,

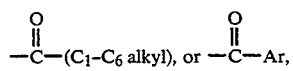

wherein Ar is optionally substituted phenyl;
$R^2$ is selected from the group consisting of pyrrolidine, hexamethyleneamino, and piperidino; or a pharmaceutically acceptable salt of solvate thereof.

1 Claim, No Drawings

OTHER PUBLICATIONS

Yang et al., "Raloxifene an Anti-Estrogen, Simulates the Effects of Estrogen in Inhibiting Bone Resorption Through Regulating TGFB—3 Expression in Bone;'-'.Am Soc. for Bone and Min. Res., Tampa Sep. 18–22, 1993.

Black et al., "Distinct, Structure-Related Profiles of Estrogenic and Anti-Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109:1981, 987–989.

Black, L. J. "Biological Actions and Binding Properites of a New Estrogen Antagosist LY117018," In: Homone Antagonists, 129–82, 1982 (M. K. Agarwal ed.) Walter de Gruyter and Co., Berlin New York.

Black et al., LY156758: A Unique Antiestrogen Displaying High Affinity for Estrogen Receptors, Negligible Estrogenic Activity and Near-Total Estrogen Antagonism in Vivo. Presented at the Fifth Annul San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Science, 32:1983. 1031–1036. 1983.

Black et al., The Relationship of the Antiestrogenic Efficacy of LY156758 to its Pharmacokinetics and Metabolism Following Oral Administration to Adult Ovariectomized Rate, Seventh Internaional Congress of Endocrinology, Quebec City, Canada, Jul. 1–7, 1984, abs. 323.

Black et al., Synthesis and Antiestrogenic Activity of [3,4-Dihydro-2(4-methoxyphenyl)-1-napthalenyl] [4-[2-pyrrolidinyl) ethoxyl]-phenyl] methanone, methanesulfonic acid salt, Journal of Medicinal Chemistry 22;1979, 962–966.

Black et al., Antiestrogens 2. Structure Activity Studies in a Series of 3-Aroyl-arylbenzo[b]thiophene Derivatives Leading to [6-Hydroxy-2-(4-hydroxyphenyl)-benzo[b]thien-3-yl][4-[2-(1-piperidinyl)ethoxy]--phenyl]methanone Hydrochloride (LY156758), a Remarkably Effective Estrogen Antagonist with Only Minimal Intrinsic Estrogeniicity, J. Med. Chem. 27(8), 1984, 1057–1066.

Bitar et al., "Suppression of Experimental Autoimmune Encephalomyelitis by the Oral Administration of Myelin Basic Protein", Cell. Immun., 112, 364–370 (1988).

Higgins et al., "Suppression of Experimental Autoimmune Encephalomyelitis by Oral Administration of Myelin Basic Protein and its Fragments", J. of Immun., 140(20), 440–445 (Jan. 15, 1988).

Khoury et al., "Oral Tolerance to Myelin Basic Protein and Natural Recovery from Experimental Autoimmune Encephalomyelitis Are Associated with Downregulation of Inflammatory Cytokines and Differential Upregulation of Transforming Growth Factor $\beta$, Interleukin 4, and Prostaglandin E Expression In the Brain", J. Exp. Med., 176,1355–1364 (Nov. 1992).

CA: 120 No: 187628x; Apr. 1994 (Guettinger et al.).

METHODS OF INHIBITING DEMYELINATING AND DESMYELINATING DISEASES

BACKGROUND OF THE INVENTION

Diseases of the myelin sheath are divided into two categories. The first category is the demyelinating or myelinoclastic diseases and the second is the dysmyelinating diseases. The myelinoclastic (demyelinating) diseases contain multiple sclerosis, myelinoclastic diffuse sclerosis, post-infectious and postvaccinal encephalomyelitis (disseminated vasculomyelinopathy), transverse myelitis, central pontine myelinolysis, and marchiafava-bignami disease.

The dysmyelinating diseases (leukodystrophies) contain metachromatic leukodystrophy, globoid cell leukodystrophy, adrenoleukodystrophy, and spongy sclerosis.

The first group (the demyelinating diseases) includes conditions in which the myelin sheath has developed normally and has a completely normal metabolic maintenance system, but in which the sheath appears to be the primary target of various conditions. In this group, two subgroups are recognized. The first one is multiple sclerosis, and some of its variants. The second group consists of the complications of various infections, principally viral, and vaccinations, which result from a misdirection of the immune response that has been activated by the infection or vaccination. Therefore, both humoral and cellular (delayed) immune factors cause the myelin sheath of either the central or the peripheral nervous systems, or of both, to become inflamed, edematous, or destroyed.

In the second category, the dysmyelinating diseases, an inborn error of metabolism causes a disturbance of myelinogenesis. The dysmyelination may result from a metabolic failure of the myelin maintenance system after normally formed myelin has been laid down.

The dysmyelinating diseases are of many types and include such disparate conditions as the leukodystrophies the gangliosidoses, such as Tay-Sachs disease; several amino-acidopathies, such as phenylketonuria and maple syrup urine disease; and probably other metabolic disturbances which in one way or another interfere with the normal development of myelin.

It should be pointed out that destruction of myelin is a nonspecific result of almost any injury to the nervous system and can be seen following physical trauma or vascular insults, with infections and neoplasms, or as a result of various intoxications. The conditions considered here are those in which such causes and factors are not recognized. Two conditions, central pontine myelinolysis and Marchiafava-Bignami disease, have been included because they fulfill the criteria of being primary diseases of myelin, although they are not easily classifiable as either variants of multiple sclerosis or instances of postinfectious or postvaccinal reactions of the nervous system.

The conditions to be described here affect primarily, but not exclusively, the central nervous system. While multiple sclerosis is a disease restricted to the central nervous system, the leukodystrophies normally also involve the peripheral nerves; the postinfectious or postvaccinal reactions may be restricted to the central nervous system (encephalomyelitis), or peripheral nervous system (Guillain-Barré syndrome) or may involve both to varying degrees.

In the experimental allergic encephalomyelitis (EAE) animal model, administration of myelin basic protein (MBP) induces EAE (Higgins et al., *J. Immunol.*, 140 (2), 440–445, Jan. 15, 1988; Bitar et al. *Cell. Immun.* 112, 364–370, (1988), and is characterized by increased levels of TGFβ and IL-5 in the brain (Khoury et al. *J. Exp. Med.*, 176, 1355–1364, Nov. 1992). Agents which induce TGFβ and other antiinflammatory cytokine(s) may be useful for the described diseases and their symptoms.

SUMMARY OF THE INVENTION

This invention provides methods of inhibiting demyelinating or dysmyelinating diseases or their symptoms comprising administering to a human in need thereof an effective amount of a compound of formula I

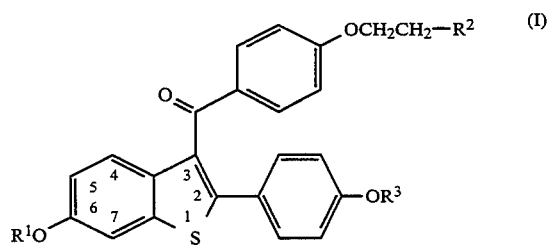

wherein $R^1$ and $R^3$ are independently hydrogen, —$CH_3$,

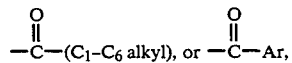

wherein Ar is optionally substituted phenyl; $R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting demyelinating or dysmyelinating diseases or their symptoms. The compounds of formula I induce the expression of TGFβ, and more specifically TGFβ-3, and this indicates usefulness for inhibition of the diseases or their symptoms.

The therapeutic and prophylactic treatments provided by this invention are practiced by administering to a human in need thereof a dose of a compound of formula I or a pharmaceutically acceptable salt or solvate thereof, that is effective to inhibit demyelinating or dysmyelinating diseases or their symptoms or its symptoms.

The term "inhibit" includes its generally accepted meaning which includes prohibiting, preventing, restraining, and slowing, stopping or reversing progression, severity or a resultant symptom. As such, the present method includes both medical therapeutic and/or prophylactic administration, as appropriate.

Raloxifene is a preferred compound of this invention and it is the hydrochloride salt of a compound of formula 1 wherein $R^1$ and $R^3$ are hydrogen and $R^2$ is 1-piperidinyl.

Generally, at least one compound of formula I is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. The term "optionally substituted phenyl" includes phenyl and phenyl substituted once or twice with $C_1$–$C_6$ alkyl $C_1$–$C_4$ alkoxy, hydroxy nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromides isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate lactate, malate maleate hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate and the like. A preferred salt is the hydrochloride salt, The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like, Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohols, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit demyelinating or dysmyelinating diseases or their symptoms according to this invention, will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed, and for a duration to effectively inhibit the disease(s) or symptom(s).

It is usually preferred to administer a compound of formula I in the form of an acid addition salt, as is customary in the administration of pharmaceuticals bearing a basic group such as the piperidino ring. For such purposes the following oral dosage forms are available.

Formulations

In the formulations which follow "Active ingredient" means a compound of formula I.

| Formulation 1: Gelatin Capsules Hard gelatin capsules are prepared using the following: | |
|---|---|
| Ingredient | Quantity (mg/capsule) |
| Active ingredient | 0.1–1000 |
| Starch, NF | 0–650 |
| Starch flowable powder | 0–650 |

-continued

Formulation 1: Gelatin Capsules
Hard gelatin capsules are prepared using the following:

| Ingredient | Quantity (mg/capsule) |
| --- | --- |
| Silicone fluid 350 centistokes | 0-15 |

The ingredients are blended, passed through a No. 45 mesh U.S. sieve, and filled into hard gelatin capsules.

Examples of specific capsule formulations of raloxifene that have been made include those shown below:

| Ingredient | Quantity (mg/capsule) |
| --- | --- |
| Formulation 2: Raloxifene capsule | |
| Raloxifene | 1 |
| Starch, NF | 112 |
| Starch flowable powder | 225.3 |
| Silicone fluid 350 centistokes | 1.7 |
| Formulation 3: Raloxifene capsule | |
| Raloxifene | 5 |
| Starch, NF | 108 |
| Starch flowable powder | 225.3 |
| Silicone fluid 350 centistokes | 1.7 |
| Formulation 4: Raloxifene capsule | |
| Raloxifene | 10 |
| Starch, NF | 103 |
| Starch flowable powder | 225.3 |
| Silicone fluid 350 centistokes | 1.7 |
| Formulation 5: Raloxifene capsule | |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

| Formulation 6: Tablets | |
| --- | --- |
| Ingredient | Quantity (mg/tablet) |
| Active ingredient | 0.1-1000 |
| Cellulose, microcrystalline | 0-650 |
| Silicon dioxide, fumed | 0-650 |
| Stearate acid | 0-15 |

The components are blended and compressed to form tablets.

Alternatively tablets each containing 0.1-1000 mg of Active ingredient are made up as follows:

| Formulation 7: Tablets | |
| --- | --- |
| Ingredient | Quantity (mg/tablet) |
| Active ingredient | 0.1-1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The Active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1-1000 mg of Active ingredient per 5 mL dose are made as follows:

| Formulation 8: Suspensions | |
| --- | --- |
| Ingredient | Quantity (mg/5 ml) |
| Active ingredient | 0.1-1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The Active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

ASSAYS

Assay 1

Experimental allergic encephalomyelitis (EAE) is an acute inflammatory autoimmune disease of the central nervous system that can be elicited in rodents and is the major animal model for the study of multiple sclerosis (MS). EAE is a systemically initiated autoimmune disease in which spinal cord homogenate or myelin basic protein (MBP) prepared in suitable adjuvants, such as complete Freund's adjuvant (CFA), is injected to activate the peripheral immune system. Rapid migration of activated T cells from peripheral blood to the CNS then occurs where they initiate a localized inflammation and subsequent demyelination. A monophasic, acute or spontaneous relapsing-remitting chronic form of the disease may develop according to the mode of sensitization, genetic background and age of the animal. Alternatively, the chronic relapsing form of EAE can also be induced by injection of MBP-specific T cell lines or clones of the helper/inducer phenotype (CD4+). The resulting demyelination closely resembles that obtained by injection of MBP.

Typically, spinal cord homogenate or MBP is mixed with CFA at a 1:1 ratio. Rodents are injected s.c. in the posterior flank at multiple sites with not less than 1 mg sensitizing protein in a final volume of approximately 100 ul. Subsequent inoculations similar to the primary, can be administered at 7 day intervals. Rodents usually demonstrate severe neurological symptoms as early as 13 days after primary inoculation with peak incidence levels of EAE being reached by 21 days. Subcutaneous injection of as few as 10e5 MBP-specific T cell line or clone cells of the CD4+ helper/inducer phenotype is also effective at inducing EAE. Compound is administered orally or s.c., before or after primary antigen inoculation, and the beneficial effects determined by evaluation of neurological symptoms associated with EAE disease progression. One can also examine cerebrospinal fluid or brain for the presence of inflammatory cells, oligoclonal IgG or increased class II expression.

ASSAY 2

Five to fifty patients are selected for the clinical study. The patients suffer from a demyelinating or desmyelinating disease which exhibits symptoms, but otherwise are in good general health. Because of the idiosyncratic and subjective nature of these disorders, the study has a placebo control group, i.e., the patients are divided into two groups, one of which receives a compound of formula 1 as the active agent and the other receives a placebo. Patients in the test group receive between 50-200 of the drug per day by the oral route. They continue this therapy for 3-12 months. Accurate records are kept as to the number and severity of the symptoms in both groups and at the end of the study these results are compared. The results are compared both between members of each group and also the results for each patient are compared to the symptoms reported by each patient before the study began.

Utility of the compounds of formula I is illustrated by the positive impact they have in at least one of the assays described above.

I claim:

1. A method of treating multiple sclerosis comprising administering to a human in need thereof an effective amount of a compound having the formula

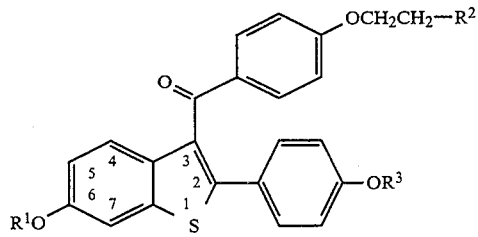

wherein $R^1$ and $R^3$ are independently hydrogen, —$CH_3$;

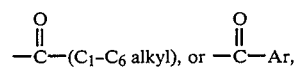

wherein Ar is optionally substituted phenyl;
$R^2$ is selected from the group consisting of pyrrolidine, hexamethylenemino, and piperidino; or a pharmaceutically acceptable salt of solvate thereof.

* * * * *